United States Patent [19]

Nakayama et al.

[11] Patent Number: 4,505,677
[45] Date of Patent: Mar. 19, 1985

[54] DRIVING METHOD AND DEVICE FOR DENTAL HAND-PIECE

[75] Inventors: Shozo Nakayama; Hiroo Watanabe, both of Kyoto, Japan

[73] Assignee: Kabushiki Kaisha Morita Seisakusho, Kyoto, Japan

[21] Appl. No.: 498,088

[22] Filed: May 25, 1983

[30] Foreign Application Priority Data

Jun. 21, 1982 [JP] Japan ............... 57-107081

[51] Int. Cl.³ .......................... A61C 1/05
[52] U.S. Cl. ................................ 433/132
[58] Field of Search ............ 433/132; 415/503, 52, 415/56, 58

[56] References Cited

U.S. PATENT DOCUMENTS 1,022,683 4/1912 Kienast .................. 415/58
4,209,293 6/1980 Sugai et al. ............. 433/132

FOREIGN PATENT DOCUMENTS

929668 6/1955 Fed. Rep. of Germany ...... 415/503
1245535 7/1967 Fed. Rep. of Germany ...... 433/132

Primary Examiner—John J. Wilson
Attorney, Agent, or Firm—Koda and Androlia

[57] ABSTRACT

This disclosure relates to an improved method for driving a hand-piece of the air drive type to improve its cutting performance, and to increase its cutting load in a low range of rotational speed in particular, and also relates to a device for practicing the method. The disclosed method employs compressed high-velocity fluid exhausted to one side of an annular space in which blades rotate after having once been jetted at said blade guided along the rotating direction of said blades and then causing it to reenter the annular space in a diagonal direction with respect to the rotational direction of the blades for further driving the running blades in the same sense. The device includes a simply machined ring-shaped adapter.

2 Claims, 9 Drawing Figures

FIG. 8

DRIVING METHOD AND DEVICE FOR DENTAL HAND-PIECE

BACKGROUND OF THE INVENTION

1. Field of the Invention

The present invention relates to improvement in a device and method for driving a dental hand-piece and more particularly to improvements in the cutting performance of a pneumatically driven dental hand-piece.

2. Prior Art

In prior-art pneumatically driven hand-pieces, the compresed high-velocity fluid (compressed air, hereinafter simply called "air") jetted out of the air outlet is exhausted through the exhaust port after driving the turbine blades, that is, after imparting a driving torque to the blades in the absense of any arrangement to reuse the air. Therefore, the hand-pieces had a drawback in that the driving torque imparted to the blades is smaller than the input amount of kinetic energy, since the air's kinetic energy potential could not be fully utilized.

The present inventors succeeded in overcoming the above-mentioned drawback in their earlier invention for which a patent is pending (Japanese Patent Publication Sho56-42941). The invention not only uses the jet air to drive the confronting blade but also causes a part of the air to act on an adjacent blade in the direction of rotation through an opening provided in the blade for additionally imparting drive torque thereto so that the total amount of torque imparted can be increased when compared with a prior art counterpart. The invention partially reuses the air jetted in the direction of rotation to increase the amount imparted to the torque.

SUMMARY OF THE INVENTION

After extensive research and experiments on the theme mentioned above, the present inventors have succeeded in providing a method for increasing the blade driving torque, especially the torque in a lower rotational speed range, compared with the prior art hand-pieces. More specifically, the air, which is jetted out of an air nozzle and directed at the confronting blade and exhausted after driving the blade to the opposite side through the space between adjacent blades (hereinafter referred to as "exhaust air"), is introduced into a newly provided adapter, and its outflowing direction is caused to agree with the blades' rotational direction (under simultaneous acceleration in the preferred embodiment) so that the air reenters the annular space in which the blades rotate diagonally with respect to their direction of rotation to further drive the running blades. The method thus represents an intensive reuse of the exhausted air. The technique therefor is different from what was disclosed in the above-mentioned prior art (Japanese Patent Publication Sho56-42941). The device for practicing the method includes substantially ring-shaped adapters(s) secured to either or both of the front and rear parts along the axis of the turbine blades. Thus, the device is simple in construction, requires no special skill in assembly.

BRIEF DESCRIPTION OF THE DRAWINGS

These and other objects and advantages and further description will be detailed in connection with the drawings in which.

DETAILED DESCRIPTION OF THE INVENTION

The present invention relates to a new method and also a device for application thereof.

The method invention is for driving a dental hand-piece wherein turbine blades 10 of a turbine rotor 1 holding a cutting tool shaft T are freely rotatable in a blade chamber 2, and compressed high-velocity fluid is jetted at each of the blades 10 in the direction of their rotation for driving the blades to rotate. The method is characterized in that the compressed high-velocity fluid exhausted to one side of an annular space 18, in which the blades 10 rotate after having once been for the first time at the blade 10, is guided along the rotating direction of the blades 10. Then the fluid is caused to reenter the blade chamber in a direction diagonal with respect to the rotating direction of the blades 10 for further driving the running blades 10 in the same direction.

The device invention, on the other hand, is an application of the above-mentioned method in which the turbine blades 10 of the turbine rotor 1 holding the cutting tool shaft are freely rotatable in a blade chamber 2, and there are provided an air feed channel 4 opening in the blade chamber 2. The compressed high-velocity fluid is jetted through the chamber 2 to reach each of the blades 10 for driving them in their rotational direction in the annular space 18 in which the blades 10 rotate. The device is characterized in that an adapter 3, which is a round ring member 30 including a fluid inlet 32 provided through a periphery 31 and a partially peripheral groove 33 formed in the periphery 31 so as to communicate with the inlet 32 at one end and with a fluid outlet 34 provided through the periphery 31 at the outer end of the groove 33, is adapted in such a manner that it is fixedly disposed in the blade chamber 2 axially adjacent to the annular space 18 in which the blades 10 rotate, and the fluid inlet 32 is located on the axially opposite side of an opening 40 of the air feed channel 4 so that the fluid inlet 32 communicates with the side of the blade 10 in the annular space 18 first in the direction of rotation.

The compressed high-velocity fluid referred to in the above is, as already mentioned, generally compressed high-velocity air. Therefore, this invention is equally applicable to hand-pieces of both air drive-mechanical journal type and air drive air-journal type. As a chuck, any of the known alternatives of metal collet chuck and sleeve chuck made of either synthetic resin or synthetic rubber may be used.

Figure 7:
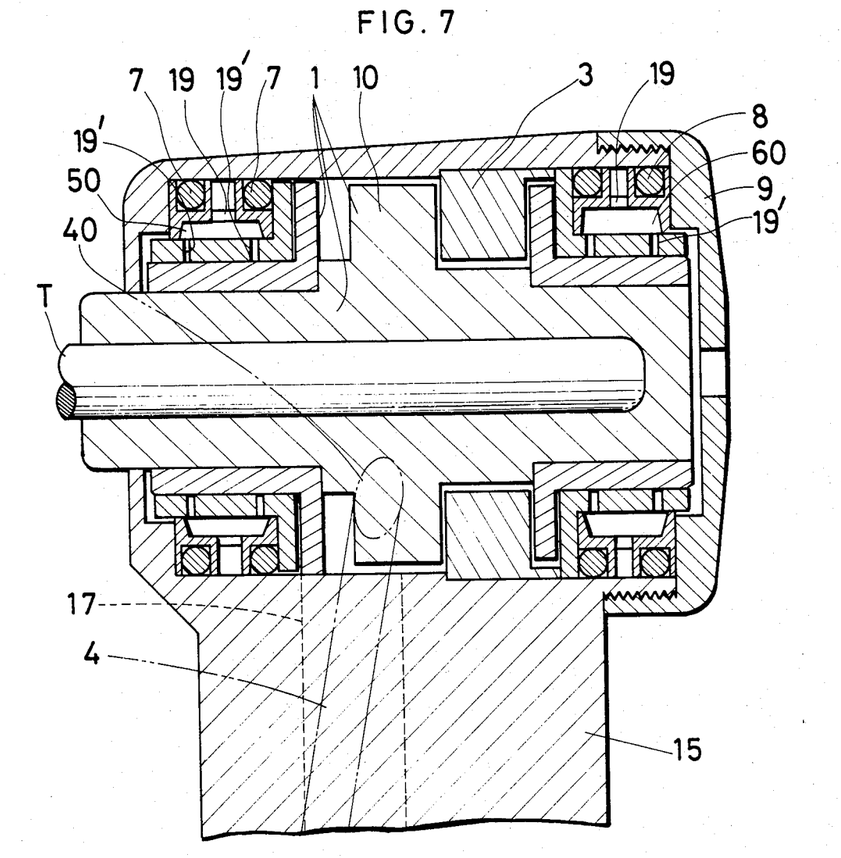
FIG. 7 is a vertical sectional view of another embodiment of the present invention, in which the invention is applied to a hand-piece of air drive-air jounal type.
Figure 8:
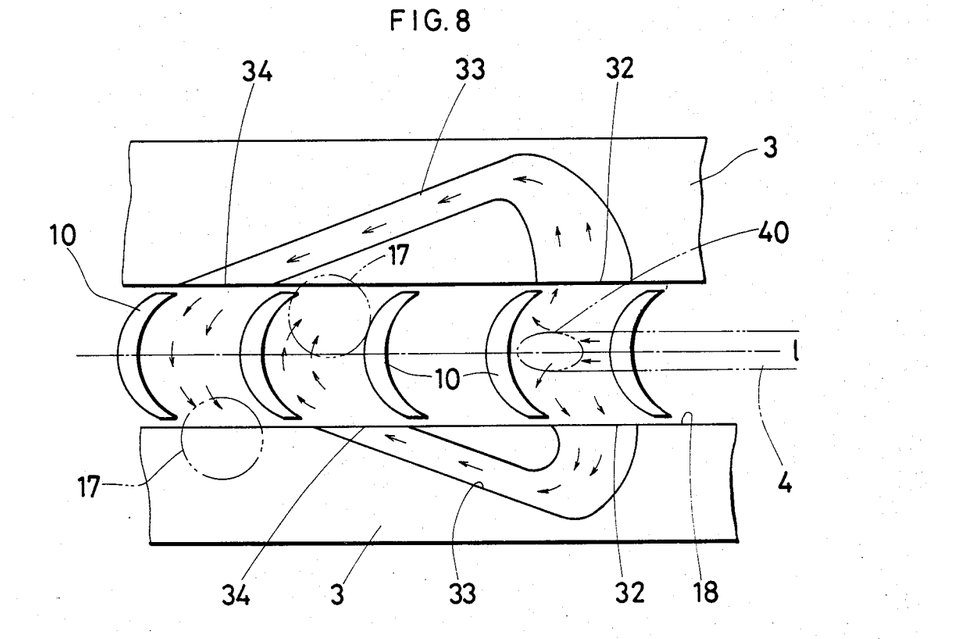
FIG. 8 is a view showing the way of function of still another embodiment of the present invention, in which the adapters are provided on both sides of the turbine blades.

The examples shown in FIGS. 1–4 is of an air drive-mechanical journal type hand-piece having a synthetic rubber chuck to which the present invention is applied (a first embodiment). The example in FIG. 7 is of the air drive-air journal counterpart having a synthetic resin chuck (a second embodiment). The example in FIG. 8 shows still another manner to use the above-mentioned adapter regardless of the journal type or chuck type.

For better understanding of the driving method of the present invention, the above-mentioned first and second embodiments will now be described in detail.

Figure 4:
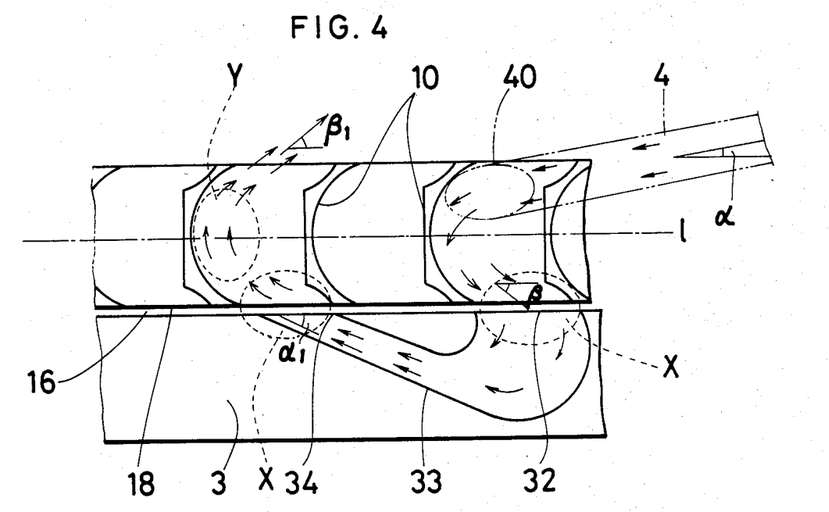
FIG. 4 is a developed view taken along the line IV—IV in FIG. 3.

In the first embodiment, a rotor shaft 11 is press-fitted at its front and rear ends with a front guide 13 and a rear guide 14. Inside of the shaft 11 is coaxially set a chuck 12 of a synthetic rubber which removably holds the cutting tool T. The roter shaft 11 is supported by ball bearing journals 5 and 6 at its front and rear ends. The rotor shaft 11, chuck 12, and the turbine blades 10 form a rotor 1. The opening 40 of the air feed channel 4 provided in a hand-piece head 15 opens in the blade chamber 2, and as shown in FIG. 4 its air jetting direction is slightly off the axis of the blade 10 confronting the opening 40 (the blade nearest at the moment to and confronting the opening 40) to one side (to the upper side in the figure). The embodiment also includes an end cover 9 and an exhaust channel 17 opening in the blade chamber 2. The above-mentioned construction is the same as the counterpart of the prior art. The present invention is characterized in that the above-mentioned adapter is adapted in the described construction.

Figure 6:
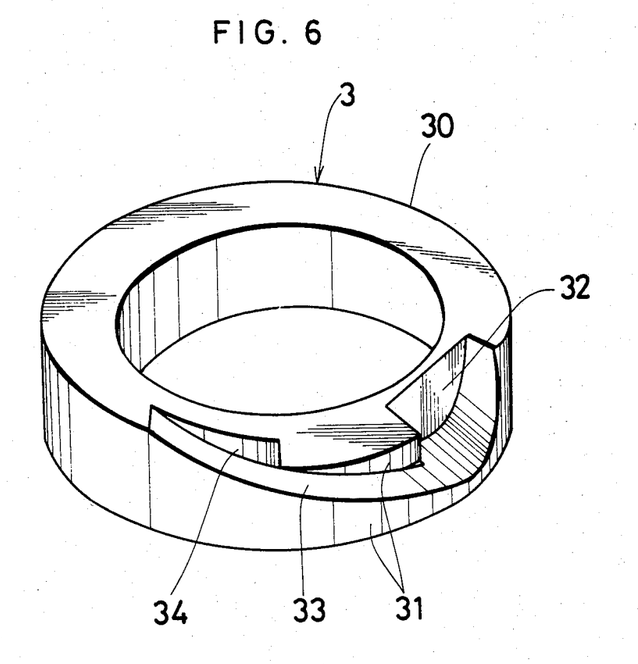
FIG. 6 is an enlarged perspective view of an adapter used in the present invention.

The adapter 3, whose construction has already been described, is shown in detail in FIG. 6. More specifically, the inlet 32 of the adapter 3 is dimensioned larger in sectional area than the outlet 34. The partially peripheral groove 33 is provided extending from the outlet 32 along the periphery 31 with its depth progressively becoming smaller from the inlet 32 toward the outlet 34. The structure of the adapter 3 is for intensively guiding the exhausted air received through the inlet 32 along the peripheral groove 33 thorough the space defined by the periphery 31 and one side of the turbine blades 10 toward the outlet 34 under simultaneous acceleration. This acceleration is made by the sectional area of the opening of the inlet 32 which is larger than that of the outlet 34 and also by the depth of the groove which gradually decreases toward the outlet 34 for the cross-sectional area of the air passage. This acceleration feature is, however, not essential for the present invention.

The relationship between the opening 40 and the inlet 32 is as shown in FIG. 4. As illustrated, the inlet 32 is located outside the annular space 18 (in which the blades rotate) on the side of the opening 40, substantially where it can effectively receive the air jetted at the blade 10 and rebounded thereby. However, the inlet 32 may be located slightly ahead of the illustrated position (toward the outlet 34), because the confronting blade 10 is driven slightly forward at the moment the air is jetted at it. Locating the inlet 32 behind the illustrated position is, however, not desirable, since an increased air loss is then caused by the gap 16 formed between the annular space 18 (rotating blades 10) and the adapter 3. The jetting direction of the air out of the outlet 34 is designed to be diagonal with respect to the width center line 1 of the annular space 18. Due to the described structure of the adapter, the air jetted out of the air feed channel 4 to the confronting blade 10 is received by the inlet 32 of the adapter 3 on the opposite side of the annular space 18, guided by the partial peripheral groove 33 and intensively through the space defined by one side of the blades 10 and the periphery 31 toward the outlet 34.

Figure 1:
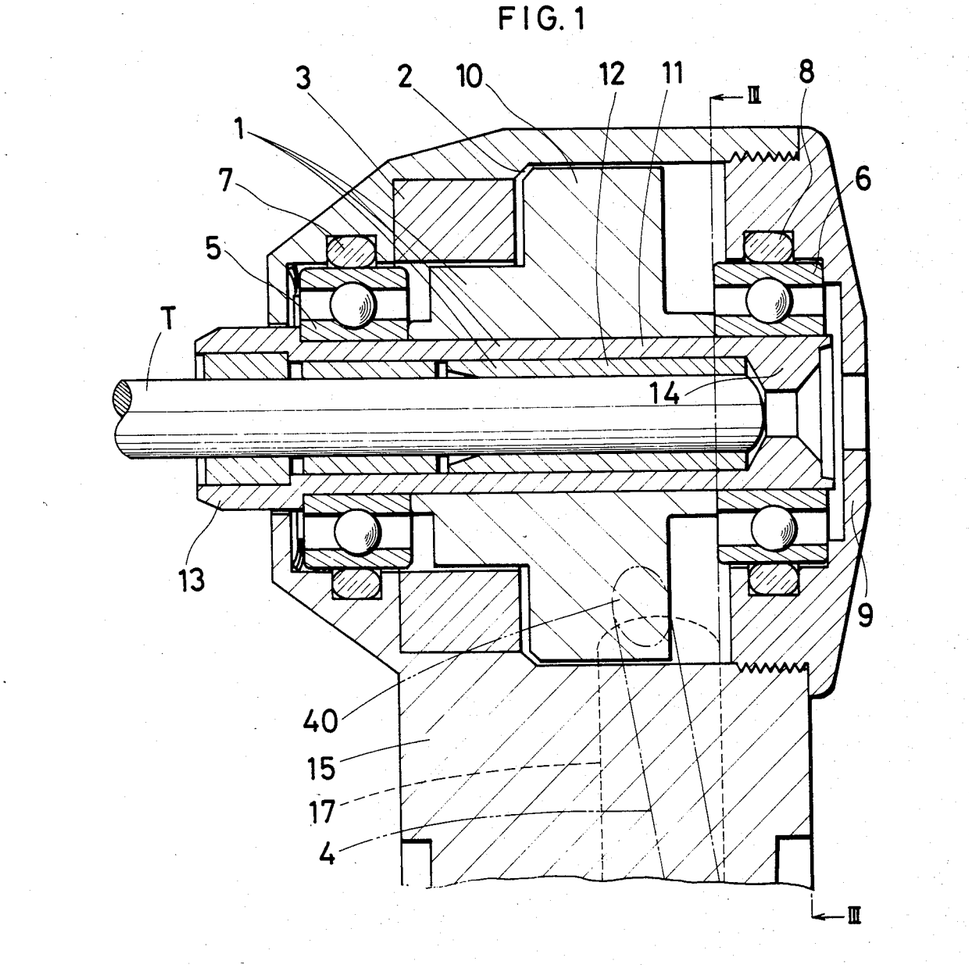
FIG. 1 is a vertical sectional side view of a dental hand-piece of air drive-mechanical journal type to which the present invention is applied.
Figure 2:
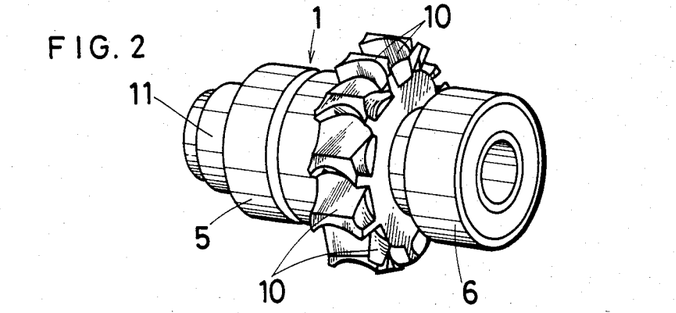
FIG. 2 is a schematic perspective view of the rotor shown in FIG. 1.
Figure 3:
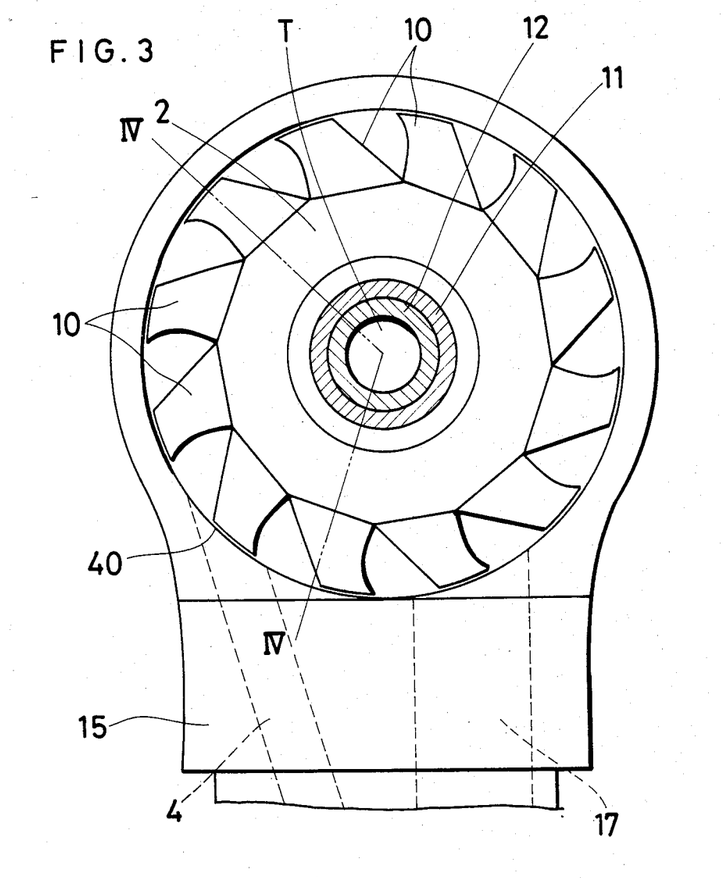
FIG. 3 is a sectional view taken along the line III—III in FIG. 1.
Figure 5:
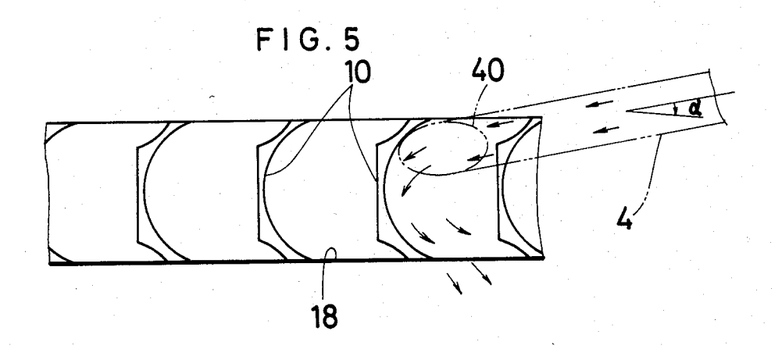
FIG. 5 is a developed view similar to FIG. 4 of a prior art hand-piece.

For better understanding of the torque increasing effect of the present invention, a developed view taken along the line IV—IV in FIG. 1 is given in FIG. 4, and a similar developed view of a prior art turbine is shown in FIG. 5. In both, the compressed air delivered by a known tube or the like through the hand-piece head 15 enters the air feed channel 4 so that its pressure energy is convered into velocity energy, and a high-velocity air stream is produced in the channel 4. This compressed high-velocity air is then jetted at the turbine blade 10, and the resulting variation is the amount of its kinetic energy and its vector components increase the torque for driving the rotor 1.

The starting torque can be calculated by the following formulae, respectively: Assuming that in FIGS. 4 and 5 the angle which the air jetting out of the air feed channel 4 makes against the width center line 1 of the annular space 18 in which the blades 10 rotate is $\alpha$; the corresponding angle when the air is exhausted after hitting the blade 10 for the first time is $\beta$; the angle which the jet direction of the air out of the outlet 34 in FIG. 4 makes against the above-mentioned width center line 1 is $\beta$; the corresponding angle when the air is exhausted after hitting the blade 10 for the second time is $\beta$; the air flow rate in the air feed channel is q (Nl/min), air velocity is $v_1$ )cm/S); the flow velocity of the first exhausted air in FIGS. 4 and 5 is $v_2$ (cm/S); the air flow velocity in the peripheral groove 33 is $v_3$; the flow velocity of the second exhaust air is $v_4$; and the distance between the center of the area of the turbine blade 10 subjected to the pneumatic force and the center of its rotation is r (cm). The torque $T_1$ for the prior art hand-piece shown in FIG. 5 can be calculated by the following equation:

$$T1 = (\sigma q/60 \cdot v_1\cos\alpha + \sigma Q_1 q/60 \cdot v_2\cos\beta) \quad (1)$$
$$\times 1/980 \times r (g \cdot cm)$$
$$= \frac{\sigma qr (v_1\cos\alpha + Q_1 v_2\cos\beta)}{60 \times 980}$$

wherein, $\sigma$ is the mass of air per 1 Nl (gr/Nl), and $Q_1$ is the leakage coefficient of air coming out of the air feed channel 4, in other words, "q-$Q_1$q(Nl/min)" is the amount of air leakage per minute through a gap 16 between the turbine blade 10 and the hand-piece head 15.

For the hand-piece of the present invention, the equation for torque calculation is as follows:

$$T_2 = [(\sigma q \times v_1\cos\alpha_1 + \sigma Q_1 q v_2\cos\beta) + \quad (2)$$
$$(\sigma Q_1 Q_2 q v_3\cos\alpha_1 + \sigma Q_1 Q_2 Q_3 q \; v_4\cos\beta_1)]$$
$$\times \frac{1}{980} \times \frac{1}{60} \times r$$

wherein $Q_2$ and $Q_3$ are the air leakage coefficeints at X and y in FIG. 4.

When for comparison the configurations of the air feed channel and the turbine blade are assumed to be identical for both equations (1) and (2) as well as the air flow rate and the feed air pressure, the values $\sigma$, $q$, $Q_1 \cdot v_1$, $v_2$, and $\beta$ are identical for both equations. Hence, the equation (2) is re-written as follows:

$$T_2 = T_1 + \frac{\sigma q r(Q_1 Q_2 Q_3 \cos\alpha_1 + Q_1 Q_2 Q_3 v_4 \cos\beta_1)}{60 \times 980} \quad (3)$$

and theroretically the increase in torque amounts to $$\frac{\sigma q r(Q_1 Q_2 v_3 \cos\alpha_1 + Q_1 Q_2 Q_3 v_4 \cos\beta_1)}{60 \times 980}$$

According to our experiments the starting torque for the hand-piece of the present invention was 13 g.cm against about 10 g.cm for the prior art counterpart having no adapter 3 with the air flow rate and feed air pressure 30 Nl/min and 2.3 kgf/cm$^2$ respectively and identical for both.

Figure 9:
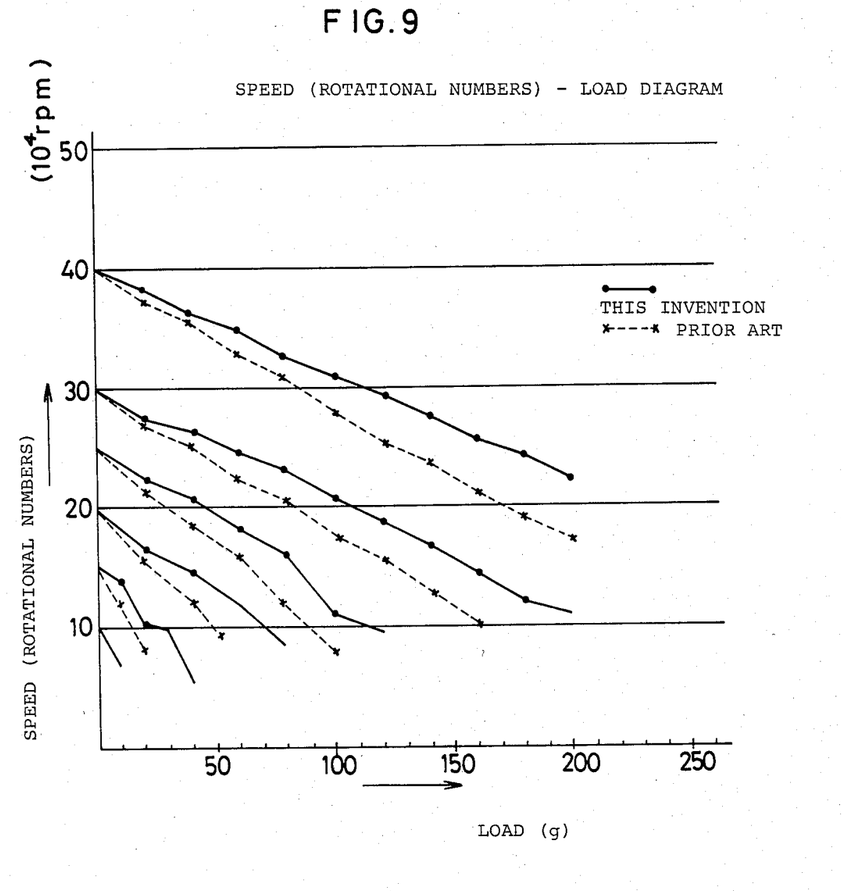
FIG. 9 is a diagram showing the comparison of the embodiment in FIG. 1 with a prior art counterpart in rotary cutting performance.

Then, the relationship between the load and rotational speed, when the both are operated without any load and at the same rotation speed, is shown in FIG. 9. In the diagram, the full-line curve shows the relationship for the hand-piece of the present invention, and the dotted curve shows the relationship for the prior art counterpart. The diagram shows that when a certain load is applied to the both running without load, the resulting decrease in the rotational speed is extremely small in the hand-piece of the present invention. And, this is still the case even in a low range rotational speed (100,000–200,000 r.p.m.). Since the cutting performance is assumed to be the results of load by rotational speed, it is apparent that the hand-piece of the present invention has very high cutting performance. Although the above-mentioned theoretical equations (1), (2), and (3) are for calculation of the torque imparted for starting hand-pieces, it is apparent experimentally from FIG. 9 that the torque imparted to keep the hand-pieces running is increased more in the present invention than in the prior art counterpart.

Although the above results all relate to the embodiment 1, the present invention is equally applicable to hand-pieces of the air drive-air journal type shown in FIG. 7.

The second embodiment shown in FIG. 7 includes essentially a prior art hand-piece (Chuck 12 is, however, a sleeve chuck made of synthetic resin.), and the adapter 3 of the first embodiment fixedly disposed axially behind the blades 10 and adjacent therto. Detailed description of this embodiment is omitted, because it is essentially the same as the first embodiment in the structure of the essential parts including the adapter 3, and only the corresponding numerals are given in the Figure. In the Figure, however, the air journals 50 and 60 are additionally shown as well as air inlets 19 and 19' for the air journal.

The third embodiment shown in FIG. 8 is not specified by the type of hand-piece but by the (relative) relation between the air feed channel and turbine blade, and the number of adapters are used. More specifically, in FIG. 8 the air feed channel 4 is disposed almost at the width center of the annular space 18 (in which the turbine blades 10 rotate); that is, the channel 4 is in agreement with the center line 1 so that the air jetted at the blade 10 is exhausted and divided to both sides at almost an equal flow rate. In this embodiment, the adapter 3 is arranged one set each on both sides of the blade 10, and the outlets 34 of the adapters 3 are positioned to be in communication with one side of the annular space 18 one behind the other along the center line thereof. In this embodiment, due to the two adapters 3, the amount of kinetic energy imparted to the turbine blades 10 is increased; hence, the torque imparted for driving the blades is further increased.

Though not illustrated, it is also possible to provide the adapters 3 in the described embodiments with a multiplicity of branched outlets 34 along the direction of rotation of the blades 10 for futther increase of the torque imparted. Also, as already mentioned above, it is confirmed that similar effects are attainable even by the use of chucks of the metal collet type. Furthermore, instead of including changes in the flow direction with simultaneous acceleration of the flow velocity of the exhaust air, the increase of the torque imparted can also be accomplished by changing the flow direction alone.

As may be well understood from the above description of the embodiments, the present invention has stemmed from the recognition that the compressed high-velocity air out of the air feed channel having once jetted at the confronting turbine blade to imprat torque thereto still has an ample reserve of kinetic as well as pressure energy as it is exhausted to one or both sides. Therefore, this invention is aimed at increasing the amount of torque imparted by changing the flow direction of the exhaust air preferably under simultaneous acceleration of its velocity for resultant utilization of the residual kinetic energy of the exhaust air for additional driving of the running blades. The effect of the present invention to increase the amount of torque imparted is proven theoretically and demonstrated experimentally, and the invention thus contributes to improvement of the applicability of hand-pieces. Furthermore, the present invention is highly practical and useful, since it only requires the use of a ring-shaped simply machined adapter, which may simply be disposed in the blade chamber and adjacent to the blades, requiring no particular assembling skill.

Having described our invention as related to the embodiments shown in the accompanying drawings, it is our intention that the invention be not limited by any of the details of the description, unless otherwise specified, but rather be construed broadly within its spirit and scope as set out in the accompanying claims.

We claim:

1. A device for driving a dental handpiece wherein turbine blades of a turbine rotor having a cutting tool shaft substantially vertically with respect to the grip portion of the handpiece having therein an air feed channel and an air exhaust channel communicating with a blade chamber are freely rotatable in a blade chamber and through said air feed channel compressed high-velocity fluid is jetted at each end of said blades to rotate the blades in their direction of rotation, said device being characterized in that an adapter comprising a round ring member, a fluid inlet provided through a periphery of said ring member, and a partial peripheral groove formed in said periphery communicating with said inlet at the one end of said groove and with a fluid outlet provided through said periphery at the other end of said groove, is adapted in such a manner that the adapter is fixedly disposed in said blade chamber axially adjacent on one side alone to an annular space in which said blades rotate with said fluid inlet located on the axially opposite side of an opening of said air feed channel so that said fluid outlet communicates with the side of said blade in said annular space ahead of the direction of rotation, and an exhaust communication channel which opens into said exhaust channel and extends peripherally is formed on the other side of said turbine blades not adjacent to said adapter.

2. A device as set forth in claim 1, wherein said fluid inlet is dimensioned larger than said fluid outlet in sectional area, and the depth of said partial peripheral groove is made progressively smaller from said fluid inlet toward said fluid outlet.

* * * * *